United States Patent
Caro

(12) 
(10) Patent No.: US 6,517,555 B1
(45) Date of Patent: Feb. 11, 2003

(54) METHOD FOR TREATING PRESBYOPIA

(75) Inventor: Nicholas C. Caro, Glenview, IL (US)

(73) Assignee: Clear Sight, Inc., Chicago, IL (US)

(*) Notice: Subject to any disclaimer, the term of this patent is extended or adjusted under 35 U.S.C. 154(b) by 271 days.

(21) Appl. No.: 09/655,377

(22) Filed: Sep. 5, 2000

(51) Int. Cl.$^7$ .............................................. A61B 17/08
(52) U.S. Cl. ...................................... 606/151; 128/898
(58) Field of Search ................................. 606/151, 157, 606/213, 215, 216, 219, 221; 623/4.1; 128/898

(56) References Cited

U.S. PATENT DOCUMENTS

| | | |
|---|---|---|
| 4,413,635 A | 11/1983 | Myer |
| 4,414,985 A | 11/1983 | Myer |
| 4,762,260 A | 8/1988 | Richards et al. |
| 4,895,289 A | 1/1990 | Richards et al. |
| 5,354,331 A | 10/1994 | Schachar |
| 5,383,898 A | 1/1995 | Sarfarazi |
| 5,489,299 A | 2/1996 | Schachar |
| 5,503,165 A | 4/1996 | Schachar |
| 5,529,076 A | 6/1996 | Schachar |
| 5,722,952 A | 3/1998 | Schachar |
| 5,731,909 A | 3/1998 | Schachar |
| 5,774,274 A | 6/1998 | Schachar |
| 5,797,932 A | 8/1998 | Min et al. |
| 6,007,578 A | 12/1999 | Schachar |
| 6,038,080 A | 3/2000 | Schachar |
| 6,051,023 A | 4/2000 | Kilmer et al. |
| 6,146,366 A | 11/2000 | Schachar |
| 6,197,056 B1 | 3/2001 | Schachar |
| 6,217,594 B1 * | 4/2001 | Hallen et al. ............... 606/157 |
| 6,246,528 B1 | 6/2001 | Schachar |

OTHER PUBLICATIONS

Mathews, Steven, "Scleral Expansion Surgery Does Not Restore Accommodation in Human Presbyopia," *Ophthalmology*, vol. 106, No. 5, pp. 873–877 (1999).

Ronald A. Schachar, MD, PhD, "Cause and Treatment of Presbyopia With a Method for Increasing the Amplitude of Accommodation," *Annals of Ophthalmology*, vol. 24, No. 12, pp. 445–452 (1992).

Schachar et al., "In vivo increase of the human lens equatorial diameter during accommodation," *American Physiological Society*, pp. R670–R676 (1996).

Schacher et al., "The Effect of Gravity on the Amplitude of Accommodation," *Annals of Ophthalmology*, vol. 26, No. 3, pp. 65–70 (1994).

Ronald A. Schachar, MD, PhD, "Zonular Function: A New Hypothesis With Clinical Implications," *Annals of Ophthalmology*, vol. 26, No. 2, pp. 36–38 (1994).

Schachar et al., "A Physical Model Demonstrating Schachar's Hypothesis of Accommodation," *Annals of Ophthalmology*, vol. 26, No. 1, pp. 4–9 (1994).

Schachar et al., "Experimental Support for Schachar's Hyopthesis of Accommodation," *Annals of Ophthalmology*, vol. 25, No. 11, pp. 404–409 (1993).

(List continued on next page.)

Primary Examiner—David O. Reip
(74) Attorney, Agent, or Firm—Cook, Alex, McFarron, Manzo, Cummings & Mehler, Ltd.

(57) ABSTRACT

A method for treating presbyopia in which the sclera is supported while substantially maintaining the spatial relationship between the ciliary muscle and the lens. The method includes making an incision in the conjunctiva to gain access to the sclera overlying the ciliary muscle. The Tenon's capsules are moved laterally to expose the sclera, and the sclera is extended outwardly. A clip is applied to the outwardly extended sclera so as to grasp a portion of the sclera, and then the Tenon's capsules are slid over the clip and the conjunctiva is closed. Preferably, four clips are applied to the sclera substantially equally spaced about the lens between the medial, inferior, lateral and superior rectus muscles. When applied to the sclera, the clips serve to prevent the sclera from buckling under the tension applied by the ciliary muscle when trying to accommodate the eye to near vision.

7 Claims, 2 Drawing Sheets

OTHER PUBLICATIONS

Ronald A. Schachar, MD, PhD, "Determination of Corneal Image–forming Properties From Corneal Topography," *American Journal of Ophthalmology*, Correspondence, vol. 115, No. 5, pp. 680–681 (1993).

Schachar et al., "Mathematic Proof of Schachar's Hypothesis of Accommodation," *Annals of Ophthalmology*, vol. 25, No. 1, pp. 5–9 (1993).

Internet Web Site, www.presbycorp.com/testindex.htm, ondated.

Neal A. Sher, MD, FACS, *Surgery for Hyperopia and Presbyopia*, Chapter 1, pp. 3–10; Chapter 4, pp. 33–36; Chapter 7, pp. 63–77; Chapter 20, pp. 195–199 (1997).

Package Labeling, Labtician Style 250, Corneal Clip (1995).

* cited by examiner

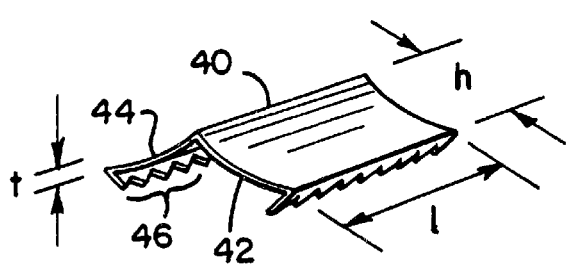
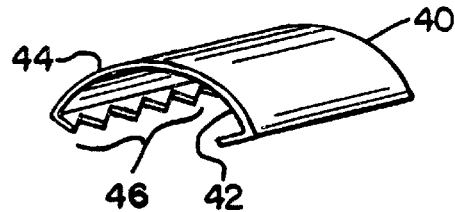
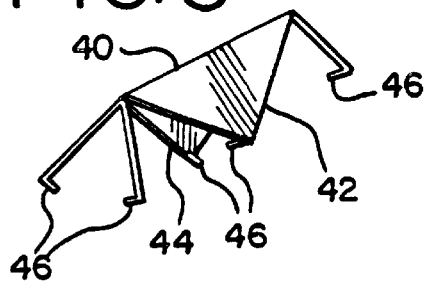
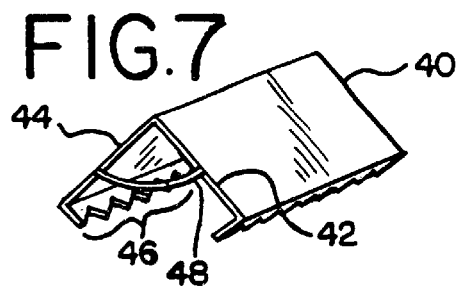
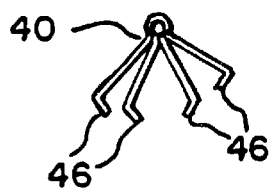
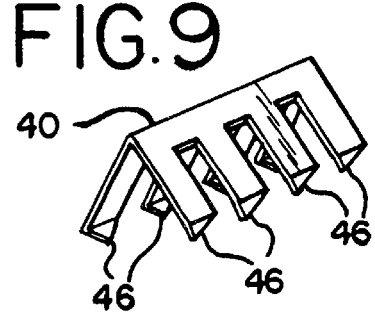
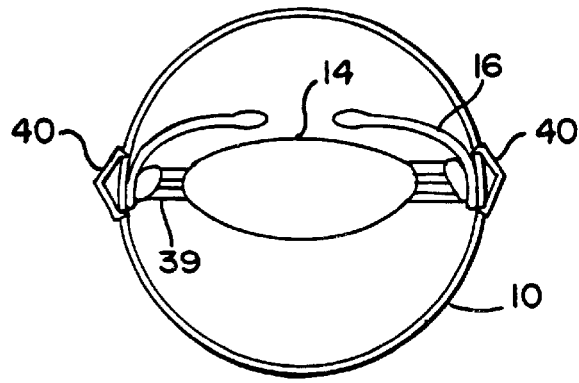

METHOD FOR TREATING PRESBYOPIA

The present invention is directed to a surgical method for treating presbyopia and to the associated devices to be used in conjunction with the method.

BACKGROUND OF THE INVENTION

Presbyopia is the nearsightedness associated with aging resulting from the failure of the accommodation mechanism of the eye. The accomodative mechanism is driven principally by parasympathetic innervation of the ciliary smooth muscle. This causes the muscle to slide forward in a unified manner and produces an inward movement of the muscle. The result is a reduction in the diameter of the ciliary muscle collar that instigates a series of events leading to an ability to see near objects clearly.

While it is clear that the capsular elasticity of the lens of the eye, i.e., the ability of the lens capsule to mold the lens, diminishes with age, the precise cause of presbyopia remains the subject of debate.

Presbyopia is most frequently treated by the use of reading glasses, bifocals, and progressive multi-focal contact lenses. However, the inconveniences associated with eyeglasses and contact lenses have prompted investigation into, and the development of, surgical techniques aimed at correcting presbyopia.

One such method is anterior ciliary sclerotomy ("ACS"). ACS is based on the theory that accommodation results primarily from ciliary body contraction, with the resulting forward movement of the lens. Its underlying rational is based on the observation that the lens constantly grows throughout life, gradually crowding the posterior chamber and eventually preventing full function of the ciliary body/zonular complex. The "crowded" state causes the reduction of lens power change with attempt at accommodation. ACS utilizes a series of symmetrical radial, partial-thickness scleral incisions to attempt to make more room for the ciliary body—which in turn allows more space for the lens—by expanding the globe in the area of the ciliary body. However, this procedure has many potential complications, ranging from infection and hemorrhaging to perforation, which could result in retinal detachment, iris injury or prolapse.

Another proposed method for surgical reversal of presbyopia is based on the theory that presbyopia results when the distance between the ciliary body and the equator of the lens and its capsule becomes less with age as a result of the normal growth of the lens. Thus, under this theory presbyopia is treated by increasing the effective working distance of the ciliary muscle. This is accomplished by implanting a series of scleral expansion bands just below the surface of the sclera and outside the cornea. The bands stretch the sclera so that the diameter of the circle describing the intersection of the plane of the ciliary body with the sclera is slightly increased. See, U.S. Pat. Nos. 5,354,331 and 5,489,399 to Schachar. However, at least one study has called into question the accuracy of the theory on which scleral expansion surgery is premised. See, Mathews, "Scleral Expansion Surgery Does Not Restore Accommodation in Human Presbyopia," Opthamology, Vol. 106, No. 5, May, 1999, pages 873–877. This study concludes that, if scleral expansion surgery does alleviate presbyopia, an explanation other than the restoration of accommodation needs to be found.

Regardless of the theory employed, there is a need for correcting presbyopia without the use of eyeglasses or contact lenses through a relatively safe and simple procedure that is easily reversible.

Accordingly, it is the principle object of the present invention to provide a surgical method for correcting presbyopia.

It is a further object to provide such a method that has a reduced potential for complications and is easily reversible.

It is a still further object of the invention to provide a clip uniquely suited for use in the treatment of presbyopia.

SUMMARY OF THE INVENTION

These objects, as well as others which will become apparent upon reference to the following detailed description and accompanying drawings, are accomplished by a method for treating presbyopia in which the sclera is supported or reinforced, while the spatial relationship between the ciliary muscle and the lens is substantially unchanged. Specifically, the method includes making an incision in the conjunctiva to gain access to the sclera overlying the ciliary muscle. The Tenon's capsules are moved laterally to expose the sclera, and the sclera is extended outwardly. A clip, or series of clips, is provided having two closeable arms for grasping the outwardly-extended sclera therebetween. The arms of the clip are closed on the sclera so as to engage a portion of the sclera, and then the Tenon's capsules are slid over the clip and the conjunctiva is closed. Preferably, four such scleral clips are applied to the sclera substantially equally spaced about the lens between the medial, inferior, lateral and superior rectus muscles. When applied to the sclera, the clips serve to prevent the sclera from buckling under tension applied by the ciliary muscle when trying to accommodate the eye to near vision.

In another aspect of the invention, a scleral clip is provided for applying to the sclera. The clip comprises two arms relatively moveable with respect to each other from an open position to a closed position. The clips have a length of no longer than approximately 5.0 to 6.0 mm so as to fit between adjacent rectus muscles. The arms may also be provided with means, such as teeth or spurs, for grasping—but not penetrating—the sclera. The arms of the clip remain in the closed position in the absence of an external force applied therebetween.

BRIEF DESCRIPTION OF THE DRAWINGS

FIGS. 3–8 are perspective views of scleral clips of various configurations to be applied to the sclera in accordance with the present invention.

FIG. 9 is a simplified diagram showing two scleral clips attached to an eye.

DETAILED DESCRIPTION

The method of the present invention is based upon a theory for the cause of presbyopia different from those set forth above. Specifically, presbyopia is caused by the failure of the ciliary body to adjust the lens diameter in order to focus images onto the retina for close objects. The ciliary muscles change the lens diameter by using the sclera as a support or fixation structure. As the sclera of the eye weakens due to age, the ciliary muscles lack the support needed in order to alter the lens diameter for focusing on close objects. Thus, in order to allow the ciliary muscle to alter the lens diameter to see close objects, the sclera must be supported or reinforced. Accordingly, a method is provided for reinforcing the sclera, so as to form a stronger and more stable support for the ciliary muscles. In effect, the sclera is strengthened, and the ciliary muscles are then able to again function properly to provide near vision.

Figure 1:
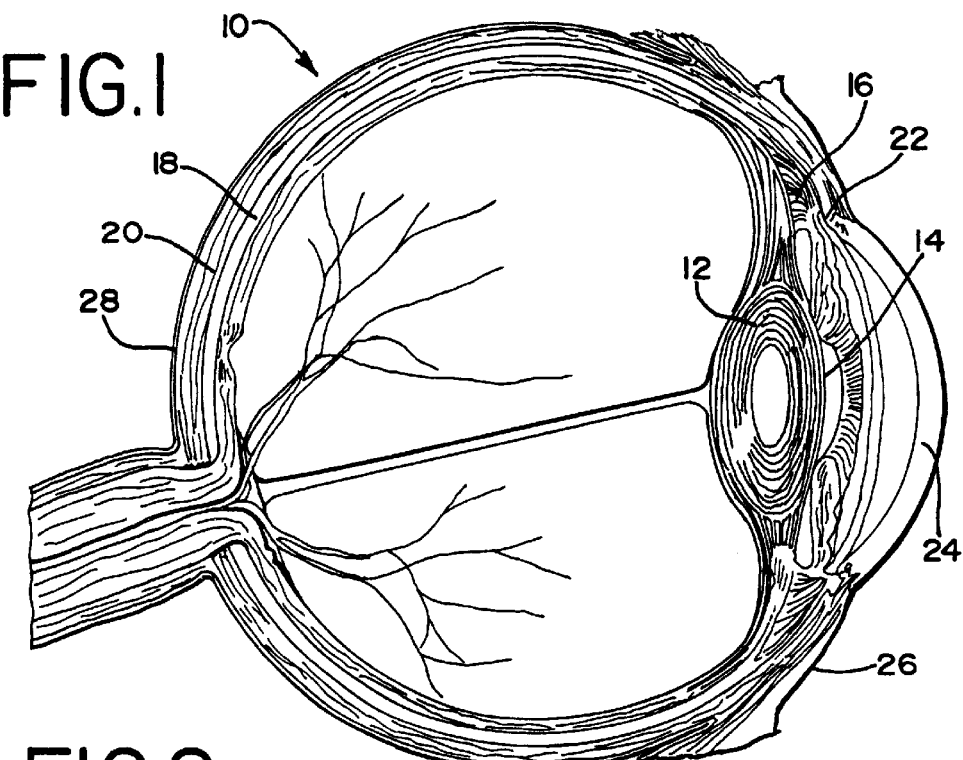
FIG. 1 is a horizontal sectional view of an eyeball.
Figure 2:
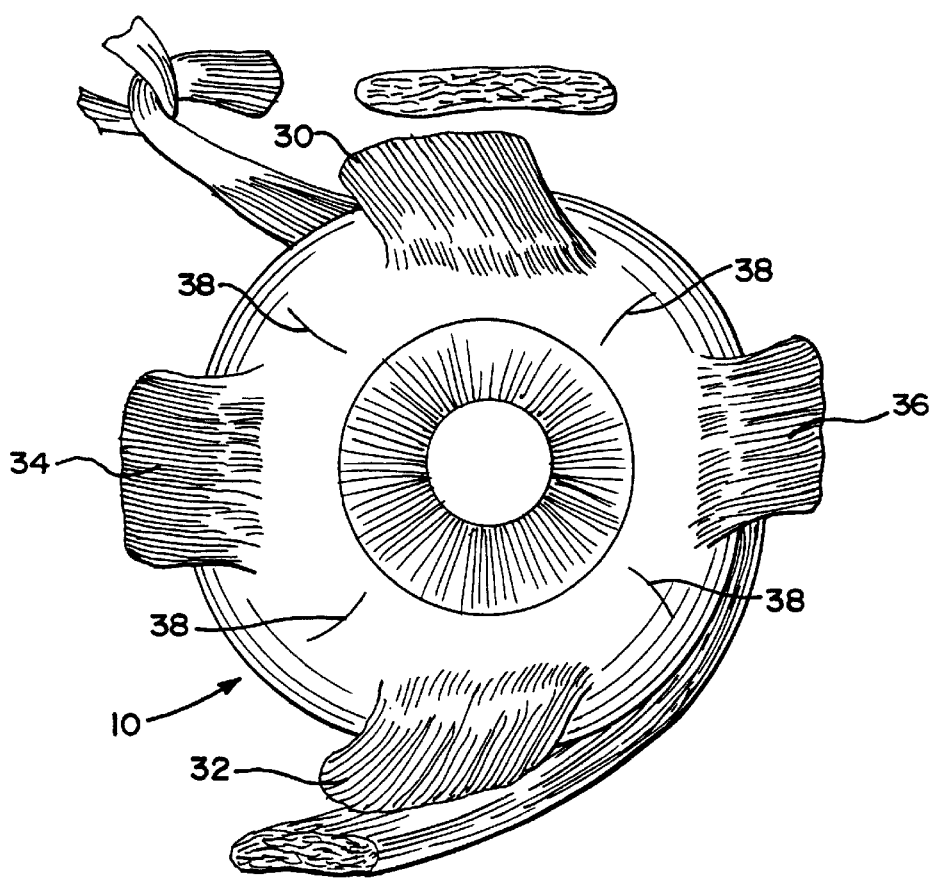
FIG. 2 is an anterior view of the eye showing the extrinsic eye muscles.

With reference to FIG. 1, there is seen a simplified sectional view of a human eye 10 having a lens 12 contained within a lens capsule 14. The ciliary body and ciliary muscle 16 are connected to the lens capsule 14 and also to the choroid 18. The sclera 20 overlies the choroid 18 and, at the front of the eye, the ciliary muscles 16, and terminates in the scleral spur 22 at the cornea 24 of the eye. The conjunctiva 26 surrounds the cornea 24 and overlies the bulbar sheath (or Tenon's capsule) 28 which, in turn, overlies the sclera 20 on the front of the eye 10. Blood is supplied to the sclera by arteries in the superior, inferior, medial and lateral rectus muscles 30, 32, 34, and 36 respectively, best seen in FIG. 2.

In the method of the invention, presbyopia is treated by first making a generally linear incision (such as incision 38 in FIG. 2) in the conjunctiva 26 to gain access to the sclera 20. The incision 38 is made radially outwardly from the cornea so as to generally bisect the area between the adjacent rectus muscles (e.g., between the superior and medial rectus muscles 30, 34 as shown by the incision 38 in FIG. 2). The Tenon's capsule 30 is then moved laterally to expose the sclera 20, and the sclera 20 is then extended outwardly. A clip 40 with two closeable arms is closed on the outwardly-extended sclera so as to put the sclera 20 under tension. The conjunctiva 26 is then closed over the clip. No suturing is needed as the conjunctive self seals. It is contemplated that four clips will be applied to the eye equally spaced about the cornea 24 between the adjacent rectus muscles.

FIG. 9 is a simplified drawing showing two clips 40 attached to the eye 10. The clips 40 grasp the sclera overlying the ciliary body 16 adjacent the iris 39. The applied clips 40 have a generally low profile, thus providing reinforcement to the sclera.

With reference to FIGS. 3–8, the clips for use in the procedure can take many different forms. In general, it is contemplated that the clip 40 will have an overall dimension of approximately 1.5–2.5 mm in heighth (h), 0.4–0.6 mm in thickness (t) and no longer than 5.0–6.0 mm in length (l). The size of the clip is constrained by the distance between the adjacent rectus muscles. Specifically, the intent is to have the clip fit between the rectus muscles, so as to not impede the flow of blood to the eye through the arteries in the rectus muscles. Thus, instead of a single clip having a length of approximately 5.0 to 6.0 mm, a series of clips can be used the sum of whose total length fits between the adjacent rectus muscles. Of course, it is anticipated that the use of a single clip of the appropriate length will allow the procedure to be performed more easily and quickly.

As can be readily appreciated, the procedure can be simply reversed by merely again gaining access to the sclera by making an incision in the conjunctiva over the clip, moving the Tenon's capsule to expose the clip, and then removing the clip. No incision into the sclera is required.

In each of the FIGS. 3–8, the clip 40 includes two arms 42, 44 joined together for relative movement to each other. On the inside portions of the clip are teeth, serrations, spurs, barbs, fingers, points 46 or other structures or projections for engaging and securely holding or gripping the sclera to the arms of the clip as it is affixed to the sclera. The teeth 46 are sized to engage the sclera, but not be of a size to penetrate the sclera (which might cause erosion of the sclera). Consequently, the teeth 46 may be as small as 20–80 μm. The clips are originally in their "open" position and then "closed" on the sclera with a forceps or other applicator, the clips remaining in their closed condition in the absence of an external force being applied to separate the arms of the clip.

The clips 40 may be made of any biocompatible material, preferably titanium, that has sufficient deformability and resilience characteristics to permit the clip to be "opened" and then remain closed when applied to the sclera.

Turning to FIG. 3, a first embodiment for the scleral clip 40 is shown in which each of the legs 42, 44 is bowed inward so as to impart some resiliency to the clip 40. Each leg 42, 44 also includes a series of teeth 46 for gripping into the sclera. The scleral clip of FIG. 4 is similar to that of FIG. 3, except resiliency is imparted to the clip 40 by having the legs 42, 44 bow outwardly.

FIG. 5 shows a further embodiment of a clip 40 that comprises a central portion in the shape of a rectangle folded along a diagonal, with a tooth 46 at each of the lower corners. A pair of staple-like members also having teeth 46 depend from the opposite ends of the rectangular portion so as to provide further means for gripping the sclera.

FIG. 6 illustrates a clip embodiment similar to FIGS. 3 and 4 except that the clip 40 includes a resilient band 48 that connects one leg to the other. The band 48 serves to keep tension on the legs 42, 44 of the clip when the teeth engage the sclera.

FIG. 7 shows a clip 40 that has a spider-like configuration with a plurality (4 shown) of legs depending from a central body, each leg terminating in a tooth 46.

FIG. 8 shows a clip 40 similar to those of FIGS. 3, 4 and 6, except that central portions of the clip 40 are removed to give it a fork-like appearance.

Thus, a method and a clip for performing the method have been provided that fully meet the objects of the present invention. While the invention has been described in terms of a preferred method and clip, there is no intent to limit the invention to the same. Instead, the invention is defined by the scope of the following claims.

What is claimed:

1. A method for treating presbyopia in an eye having a lens, ciliary muscles supporting the lens, and sclera overlying the ciliary muscles by providing support to the sclera while substantially maintaining the spatial relationship between the ciliary muscle and the lens.

2. The method of claim 1 wherein the sclera is supported at at least two locations overlying the ciliary muscles.

3. The method of claim 1 wherein the sclera is supported at four locations substantially equally spaced about the lens.

4. The method of claim 1, 2, or 3 wherein the sclera is supported by a clip that grips the sclera.

5. A method of treating presbyopia in a eye having a lens, ciliary muscles suspending the lens, sclera overlying the ciliary muscles and conjunctiva overlying the sclera comprising the steps of:

making an incision in the conjunctiva to gain access to the sclera overlying the ciliary muscle;

extending the sclera outwardly;

providing a clip with two closeable arms for engaging the sclera;

closing the arms of the clip on the outwardly-extended portion of the sclera so as to grasp a portion of the sclera therebetween;

closing the conjunctiva over the clip.

6. The method of claim 5 wherein a plurality of clips are applied to the sclera.

7. The method of claim 6 wherein at least four clips are applied to the sclera substantially equally spaced about the lens.

* * * * *